(12) United States Patent
Bulu

(10) Patent No.: US 10,586,017 B2
(45) Date of Patent: Mar. 10, 2020

(54) AUTOMATIC GENERATION OF UI FROM ANNOTATION TEMPLATES

(71) Applicant: INTERNATIONAL BUSINESS MACHINES CORPORATION, Armonk, NY (US)

(72) Inventor: Hakan Bulu, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/692,925

(22) Filed: Aug. 31, 2017

(65) Prior Publication Data

US 2019/0065682 A1 Feb. 28, 2019

(51) Int. Cl.
| | |
|---|---|
| *G06K 9/00* | (2006.01) |
| *G06F 19/00* | (2018.01) |
| *G06F 17/24* | (2006.01) |
| *G16H 40/63* | (2018.01) |
| *G06F 9/451* | (2018.01) |
| *G16H 30/20* | (2018.01) |
| *G16H 30/40* | (2018.01) |
| *G06F 8/38* | (2018.01) |

(52) U.S. Cl.
CPC ............. *G06F 19/321* (2013.01); *G06F 8/38* (2013.01); *G06F 9/451* (2018.02); *G06F 17/241* (2013.01); *G06F 17/248* (2013.01); *G16H 30/20* (2018.01); *G16H 30/40* (2018.01); *G16H 40/63* (2018.01)

(58) Field of Classification Search
CPC ...... G06F 19/321; G06F 9/451; G06F 17/241; G16H 40/63
See application file for complete search history.

(56) References Cited

U.S. PATENT DOCUMENTS

| | | | |
|---|---|---|---|
| 7,793,217 B1 | 9/2010 | Kim et al. | |
| 9,880,989 B1* | 1/2018 | Cadabam | G06F 17/241 |
| 2006/0265640 A1* | 11/2006 | Albornoz | G06F 17/2247 |
| | | | 715/234 |
| 2010/0011282 A1* | 1/2010 | Dollard | G06F 17/241 |
| | | | 715/233 |
| 2011/0041140 A1* | 2/2011 | Harm | G06F 9/4843 |
| | | | 719/318 |
| 2011/0320970 A1* | 12/2011 | Charrad | G06F 9/451 |
| | | | 715/765 |
| 2012/0159391 A1* | 6/2012 | Berry | A61B 5/4824 |
| | | | 715/823 |

(Continued)

FOREIGN PATENT DOCUMENTS

| | | |
|---|---|---|
| WO | 2007050962 A2 | 5/2007 |
| WO | 2015114485 A1 | 8/2015 |

*Primary Examiner* — Amara Abdi
(74) *Attorney, Agent, or Firm* — Erik Huestis; Stephen Kenny; Foley Hoag

(57) ABSTRACT

Automatic generation of user interfaces from annotation templates is provided. In various embodiments, a medical imaging study is retrieved from a data store. At least one characteristic of the medical imaging study is determined. Based on the at least one characteristic, an annotation configuration is selected. Based on the annotation configuration, an annotation user interface is generated for annotation of the medical imaging study. The annotation user interface and the medical imaging study is displayed to a user.

17 Claims, 3 Drawing Sheets

(56) References Cited

U.S. PATENT DOCUMENTS

| | | | | |
|---|---|---|---|---|
| 2014/0104311 A1* | 4/2014 | Park | .................. | G06F 19/321 |
| | | | | 345/629 |
| 2015/0209978 A1* | 7/2015 | Snyder | ............... | B29B 17/0026 |
| | | | | 264/308 |
| 2015/0320365 A1 | 11/2015 | Schulze et al. | | |
| 2016/0350484 A1* | 12/2016 | Son | .................. | G06F 19/321 |
| 2018/0292958 A1* | 10/2018 | Martinez | ............... | G06F 3/0484 |

\* cited by examiner

AUTOMATIC GENERATION OF UI FROM ANNOTATION TEMPLATES

BACKGROUND

Embodiments of the present disclosure relate to medical image annotation, and more specifically, to automatic generation of user interfaces from annotation templates.

BRIEF SUMMARY

According to embodiments of the present disclosure, methods of and computer program products for medical image annotation are provided. In various embodiments, a medical imaging study is retrieved from a data store. At least one characteristic of the medical imaging study is determined. Based on the at least one characteristic, an annotation configuration is selected. Based on the annotation configuration, an annotation user interface is generated for annotation of the medical imaging study. The annotation user interface and the medical imaging study is displayed to a user.

DETAILED DESCRIPTION

In medicine, each domain, body part, and feature of interest has its own unique characteristics. Thus, it is not practical to use the same annotation template both for mammography and cardiology. Accordingly, a medical image annotation system requires many annotation templates for each type of annotation. The present disclosure provides for generation of annotation user interfaces automatically to enable a user to make annotations in manner tailored to the imagery at hand.

In various embodiments, an annotation template is described using a configuration file. In some embodiments, the configuration file is a JSON file. An exemplary JSON excerpt is provided below in Inset 1.

Inset 1

```
{
    "templatename": "Semi-automatic Aortic Valve Measurements",
    "templateID": "a92d82c6-0b20-424a-b88c-55e877ee2280",
    "label": "Valve Measurements",
    "fields": [
    |  {
    |  |  "fieldname": "KeyPoints",
    |  |  "label": "Key Points",
    |  |  "description": "Key Points",
    |  |  "type": "RadioButton",
    |  |  "values": [
    |  |  |  {
    |  |  |  |  "label": "Peak of QRS complex (ECG)",
    |  |  |  |  "value": "QRS"
    |  |  |  },
    |  |  |  {
    |  |  |  |  "label": "End of T-wave (ECG)",
    |  |  |  |  "value": "T-wave"
```

Inset 1 -continued

```
    |  |  |  }
    |  |  ]
    |  },
    |  {
    |  |  "fieldname": "CalculatedResults",
    |  |  "label": "Calculated Results",
    |  |  "description": "Calculated Results",
    |  |  "type": "TextField",
    |  |  "values": [
    |  |  |  {
    |  |  |  |  "value": "EjectionFraction",
    |  |  |  |  "label": "Ejection Fraction:",
    |  |  |  |  "unit": "%"
    |  |  |  }
    |  |  ]
    |  },
    |  {
    |  |  "fieldname": "Segmentation"
```

In various embodiments, a user interface is generated at runtime from the configuration file. In some embodiments, the user interface is generated by a javascript class. In some embodiments, the generated user interface is provided in HTML. In some embodiments, the user interface is provided for rendering by a web browser as part of a medical imagery annotation system.

By adopting these approaches, flexibility is provided in medical imagery annotation systems. For example, in embodiments leveraging JSON, javascript, and HTML a user can create a customized template without the need to install any additional client side applications. A JSON file can be edited using standard text editors, and template changes may be reflected immediately via a web browser.

Figure 1:
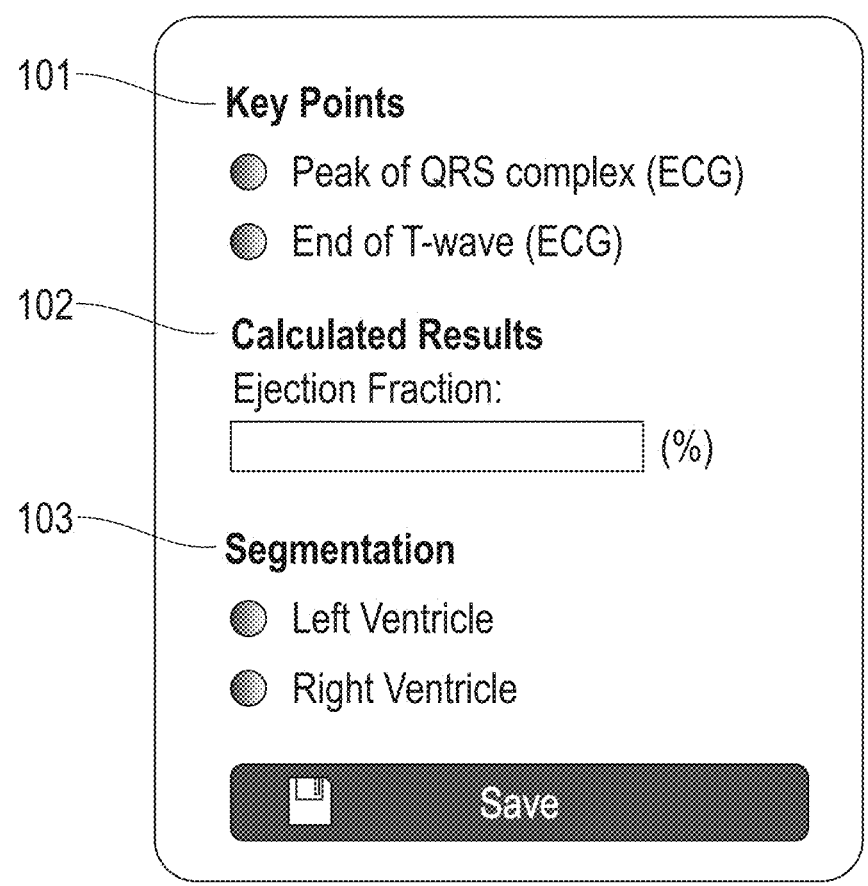
FIG. 1 illustrates an exemplary user interface according to embodiments of the present disclosure.

With reference now to FIG. 1, an exemplary user interface generated from the configuration of Inset 1 is provided. In this example, a plurality of field descriptions 101, 102, 103 are provided. Each field has an associated control for entry of relevant data as defined in the template configuration. For example, while the Key Points field 101 provides predefined options for user selection, Calculated Results field 102 allows a user to enter a numeric value with an associated unit.

To provide robust annotation of large image datasets, systems according to the present disclosure are not limited with respect to data types, can operate via a web application, and provide significant ease of use. According to various embodiment of the present disclosure, a platform is provided for creation and organization of image collections from large image repositories for the purpose of training and testing image analytics algorithms and products. Collections are assigned to registered clinical experts for annotation. These annotations may serve as ground truth for training and testing of analytics or may be part of a clinical workflow.

It will be appreciated that various imaging studies may be drawn from a PACS system for annotation according to the present disclosure. A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

In various embodiments, a library of template configurations may be maintained on the client side or the server side. In some embodiments, one of the configurations from the library is selected at runtime based on characteristics of the imagery being annotated. For example, the type of image, modality, domain, body part represented, feature of interest present, or patient information may determine the template selected. In some embodiments, a plurality of templates is maintained on the server side while individual user customizations are maintained at the client side. In some embodiments, each user has a profile maintained on the server that includes customized template configurations. In some embodiments, the templates each have associated image characteristics to enable matching between a given study and the appropriate template.

Figure 2:
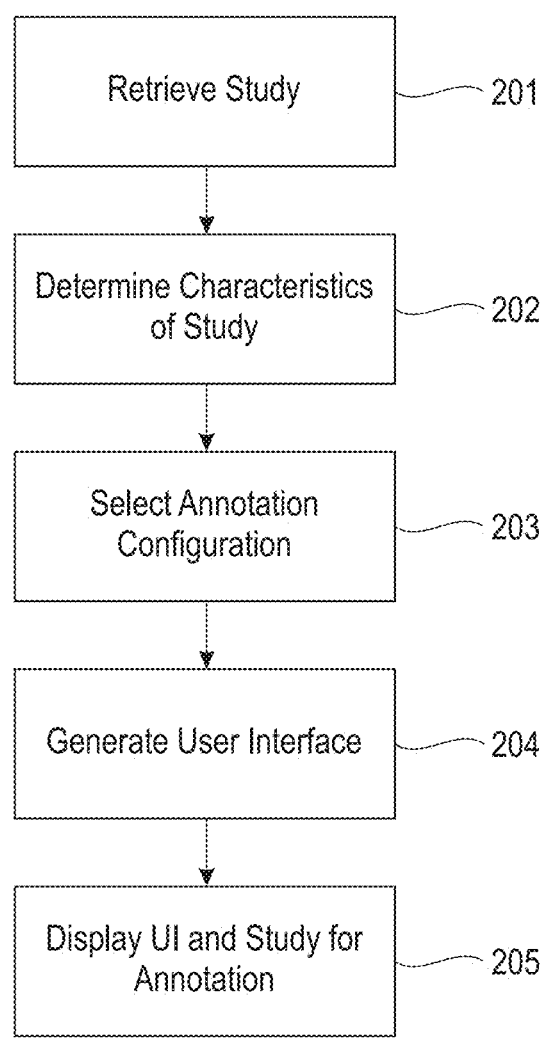
FIG. 2 illustrates a method for user interface generation according to embodiments of the present disclosure.

With reference now to FIG. 2 a method for user interface generation is illustrated according to embodiments of the present disclosure. At 201, a medical imaging study is retrieved from a data store. At 202, at least one characteristic of the medical imaging study is determined. At 203, based on the at least one characteristic, an annotation configuration is selected. At 204, based on the annotation configuration, an annotation user interface is generated for annotation of the medical imaging study. At 205, the annotation user interface and the medical imaging study is displayed to a user.

In some embodiments, the data store comprises a PACS. In some embodiments, the annotation user interface is displayed via a web browser. In some embodiments, the annotation configuration comprises a JSON file. In some embodiments, the at least one characteristic comprises a type of image, modality, domain, body part represented, feature of interest present, or patient information. In some embodiments, the annotation configuration is selected from a plurality of configurations, each having associated image characteristics. In some embodiments, the annotation user interface is generated by a web browser at runtime. In some embodiments, the annotation user interface is generated by a client-side script, such as for example a javascript.

Figure 3:
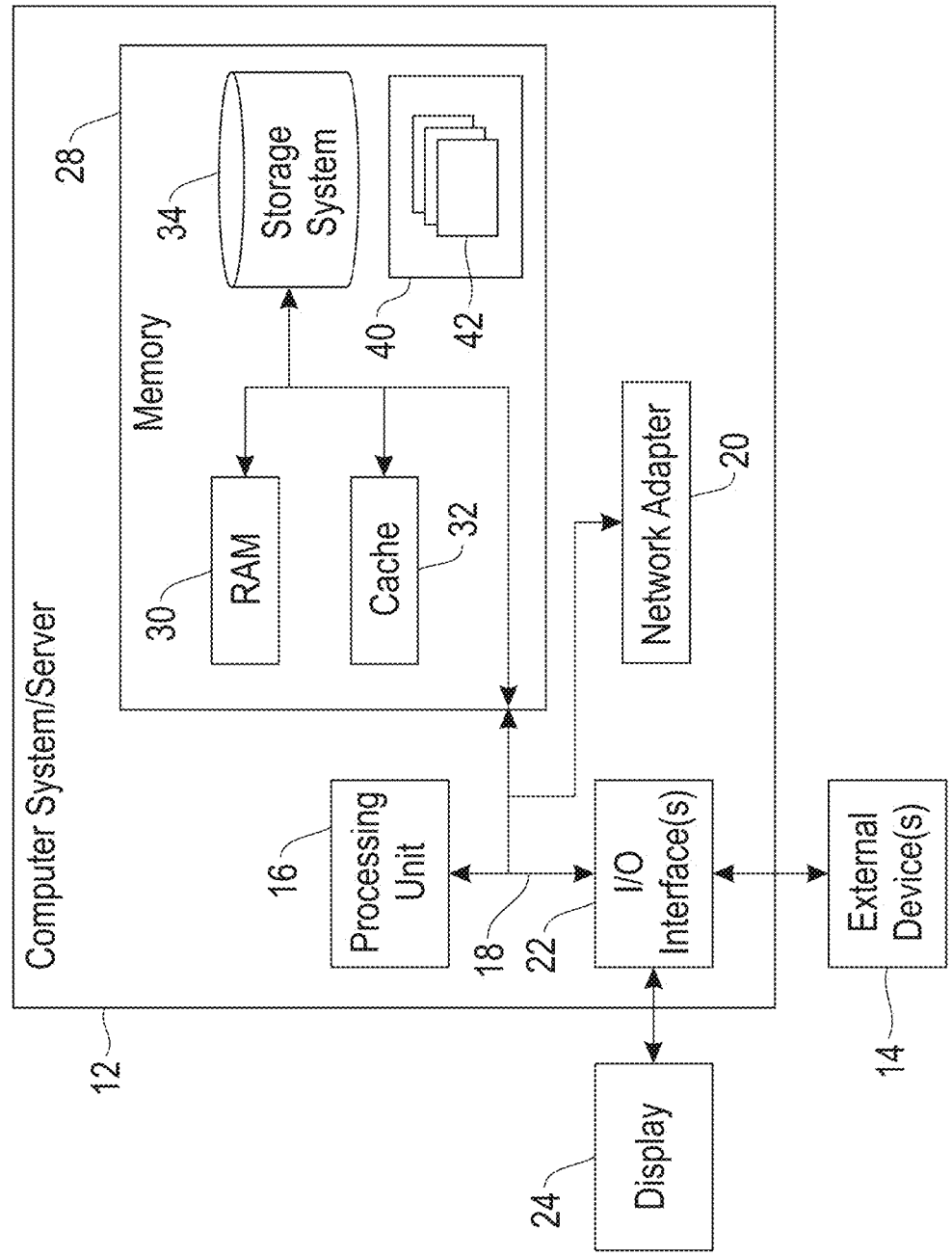
FIG. 3 depicts a computing node according to an embodiment of the present invention.

Referring now to FIG. 3, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatic user interface generation by a computer, the method comprising:
    retrieving a medical imaging study from a data store;
    determining at least one characteristic of the medical imaging study by the computer;
    based on the at least one characteristic, automatically retrieving by the computer, at runtime, an annotation configuration from a library,
        the library comprising a plurality of annotation configurations, each of the annotation configurations comprising a plurality of field descriptions and control types;
    based on the annotation configuration, generating by the computer an annotation user interface for annotation of the medical imaging study, the annotation user interface comprising a plurality of controls corresponding to the plurality of field descriptions and control types of the annotation configuration;
    displaying the annotation user interface and the medical imaging study to a user.

2. The method of claim 1, wherein the data store comprises a PACS.

3. The method of claim 1, wherein the annotation user interface is displayed via a web browser.

4. The method of claim 1, wherein the annotation configuration comprises a JSON file.

5. The method of claim 1, wherein the at least one characteristic comprises a type of image, modality, domain, body part represented, feature of interest present, or patient information.

6. The method of claim 1, wherein the annotation configuration is selected from a plurality of configurations, each having associated image characteristics.

7. The method of claim 1, wherein the annotation user interface is generated by a web browser at runtime.

8. The method of claim 7, wherein the annotation user interface is generated by a script.

9. A system for automatic user interface generation by a computer, the system comprising:
    a data store;
    a computing node comprising a computer readable storage medium having program instructions embodied therewith, the program instructions executable by a processor to cause the processor to perform a method comprising:
        retrieving a medical imaging study from a data store;
        determining at least one characteristic of the medical imaging study by the computer;
        based on the at least one characteristic, automatically retrieving by the computer, at runtime, an annotation configuration from a library,
            the library comprising a plurality of annotation configurations, each of the annotation configurations comprising a plurality of field descriptions and control types;
        based on the annotation configuration, generating by the computer an annotation user interface for annotation of the medical imaging study, the annotation user interface comprising a plurality of controls corresponding to the plurality of field descriptions and control types of the annotation configuration;
        displaying the annotation user interface and the medical imaging study to a user.

10. A computer program product for automatic user interface generation by a computer, the computer program product comprising a non-transitory computer readable storage medium having program instructions embodied therewith, the program instructions executable by a processor to cause the processor to perform a method comprising:
    retrieving a medical imaging study from a data store;
    determining at least one characteristic of the medical imaging study by the computer;
    based on the at least one characteristic, automatically retrieving by the computer, at runtime, an annotation configuration from a library,
        the library comprising a plurality of annotation configurations, each of the annotation configurations comprising a plurality of field descriptions and control types;
    based on the annotation configuration, generating by the computer an annotation user interface for annotation of the medical imaging study, the annotation user interface comprising a plurality of controls corresponding to the plurality of field descriptions and control types of the annotation configuration;
    displaying the annotation user interface and the medical imaging study to a user.

11. The computer program product of claim 10, wherein the data store comprises a PACS.

12. The computer program product of claim 10, wherein the annotation user interface is displayed via a web browser.

13. The computer program product of claim 10, wherein the annotation configuration comprises a JSON file.

14. The computer program product of claim 10, wherein the at least one characteristic comprises a type of image, modality, domain, body part represented, feature of interest present, or patient information.

15. The computer program product of claim 10, wherein the annotation configuration is selected from a plurality of configurations, each having associated image characteristics.

16. The computer program product of claim 10, wherein the annotation user interface is generated by a web browser at runtime.

17. The computer program product of claim 16, wherein the annotation user interface is generated by a script.

* * * * *